United States Patent
Cox et al.

(10) Patent No.: US 7,811,297 B2
(45) Date of Patent: Oct. 12, 2010

(54) ACTUABLE STRUCTURES AND METHODS OF FABRICATION AND USE

(75) Inventors: Brian Nelson Cox, Thousand Oaks, CA (US); Julia Jeannine Mack, Encino, CA (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 804 days.

(21) Appl. No.: 11/635,828

(22) Filed: Dec. 8, 2006

(65) Prior Publication Data

US 2007/0151202 A1  Jul. 5, 2007

Related U.S. Application Data

(60) Provisional application No. 60/597,568, filed on Dec. 10, 2005.

(51) Int. Cl.
*A61F 2/06* (2006.01)
(52) U.S. Cl. ............... 606/151; 623/14.13; 623/917; 623/918; 623/919
(58) Field of Classification Search ............ 310/26, 310/328; 606/213; 623/915–919, 14.13; 603/151
See application file for complete search history.

(56) References Cited

U.S. PATENT DOCUMENTS 4,032,929 A * 6/1977 Fischbeck et al. ............ 347/42

2004/0098042 A1 * 5/2004 Devellian et al. ........... 606/213
2004/0136905 A1 * 7/2004 Kent et al. .................. 424/1.11
2005/0245658 A1   11/2005 Mehrotra et al.

OTHER PUBLICATIONS

Stankus et al.; Microintegrating smooth muscle cells into a biodegradable elastomeric fiber matrix, Biomaterials 2006;27:735-744.
Stitzel, et al.; Controlled Fabrication of a Biological Vascular Substitute, Biomaterials 2006;27:1088-1094.
Wang, et al.; Precision Extruding Deposition and Characterization of Cellular Poly-∈-caprolactone tissue scaffolds 2004;10(1):42-49.

* cited by examiner

*Primary Examiner*—Quyen Leung
*Assistant Examiner*—Terrance Kenerly
(74) *Attorney, Agent, or Firm*—Glenn H. Lenzen; Polsinelli Shughart PC

(57) ABSTRACT

An actuable truss with ordered or disordered planar or strut elements or pore walls may be seeded with tissue cells, wherein application of a magnetic field may result in mechanical strain on the cells and increased fluid flow in and out of the truss structure. Modified polymers, such as $\gamma\text{-Fe}_2\text{O}_3$/PLGA, may be used to form actuable scaffolds suitable for tissue engineering. It is also disclosed a device with a trap-door that may be remotely actuated by applying a magnetic field. Such a device may be employed to deliver and control the release of other micro-devices or materials such as drugs to a specific location inside the body of a human or an animal.

13 Claims, 9 Drawing Sheets

FIG. 4

$$\varepsilon_z = \frac{a^2}{h^2}\bar{\eta}\cos\alpha \qquad \varepsilon_x = \frac{a^2}{h^2}\bar{\eta}\frac{\sin^2\alpha}{\cos\alpha} \qquad \bar{\eta} = \frac{\mu_0 M H_x}{E} \qquad (1)$$

$$E_z = \frac{2E\sin\alpha}{\cos^4\alpha}\left(\frac{h}{a}\right)^4 \qquad (2)$$

$$F_x = 4h\mu_0 MH\sin^2\alpha \qquad F_z = 4h\mu_0 MH\sin\alpha\cos\alpha \qquad (3)$$

$$F = \mu\cdot\frac{dB}{dx} \qquad (4)$$

$$T = \mu\times B \qquad (5)$$

FIG. 6
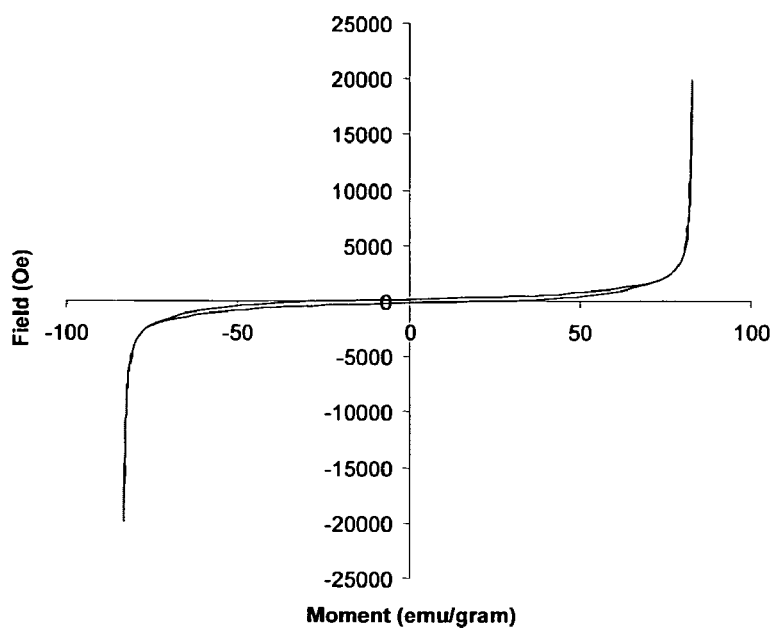
γ-Fe$_2$O$_3$ powder
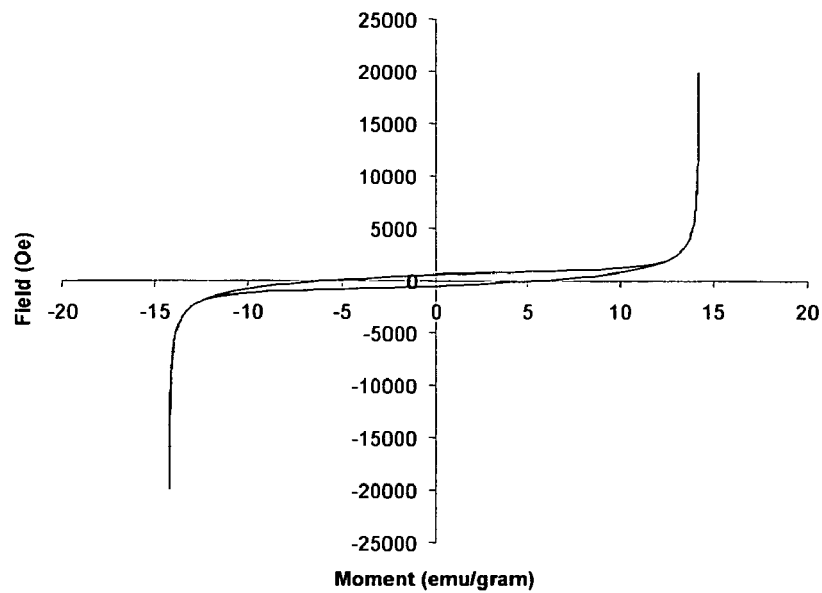
30 wt. % γ-Fe$_2$O$_3$/PLGA

ACTUABLE STRUCTURES AND METHODS OF FABRICATION AND USE

RELATED MATERIALS

This application claims priority to U.S. provisional patent application 60/597,568 filed Dec. 10, 2005, the content of which is hereby incorporated into this application by reference.

FIELD

The disclosure relates to actuable structures and devices where the actuation or physical motion is driven by a remotely applied magnetic field. More particularly, it relates to the fabrication and use of actuable structures for the support and stimulation of cell growth and differentiation. The actuable structure or device can be implanted in the body and stimulated by a field applied from outside the body. The disclosure also relates to a device useful for delivery and controlled release of materials or micro-devices in vivo.

BACKGROUND

Highly organized and biologically functional engineered tissues are desirable in repairing or replacing diseased tissues. Much effort has been focused on developing biodegradable polymer scaffolds suitable for tissue engineering. An ideal scaffold should mimic the structural and purposeful profile of materials found in the natural extracellular matrix (ECM) architecture. Biocompatible and biodegradeable polymers are common materials for scaffold fabrication. Nanofibers of biocompatible polymers prepared by electrospinning are considered a favorable material for tissue engineering scaffolds due to their high surface area to volume ratio desirable for enhanced cell attachment. Biocompatible polymers include poly(L-lactic-co-epsilon-caprolactone) (P(LLA-CL)) and poly(D,L-lactide-co-glycolide) (PLGA) (See Lee et al., Nanofiber alignment and direction of mechanical strain affect the ECM production of human ACL fibroblast, *Biomaterials*, 26: 1261 (2004) and Xu et al., Aligned biodegradable nanofibrous structure: a potential scaffold for blood vessel engineering, *Biomaterials* 25:877 (2004)).

In addition to the physical and/or chemical properties of the scaffold materials, mechanical forces may also play an important role in cell growth and tissue formation. Several investigators have reported that cyclic mechanical stretch increases ECM production in cultured fibroblasts on flexible membranes (See e.g., E. C. Breen, Mechanical strain increases type I collagen expression in pulmonary fibroblasts in vitro. *J Appl Physiol* 88: 203 (2000)). It has also been reported that mechanical strain may stimulate the release of a growth factor (See e.g., Sudhir et al., Mechanical strain stimulates a mitogenic response in coronary vascular smooth muscle cells via release of basic fibroblast growth factor. *Am J Hypertens.* 14:1128 (2001)). Moreover, mechanical strain may affect the orientation of the cytoskeleton, which, in turn, determines the orientation, alignment and mobility of a cell (See Ingber, Cellular tensegrity: exploring how mechanical changes in the cytoskeleton regulate cell growth, migration, and tissue pattern during morphogenesis. *Int Rev Cytol* 150: 173 (1994)). Therefore, mechanical strain is instrumental in the formation of many types of tissues, such as connective and muscle tissues.

Fluid flow is another important factor in tissue engineering. Cells require nutrients and oxygen to grow, and waste materials and dead cells must be promptly removed to avoid deleterious effects on healthy cells. In tissue engineering, however, these tasks are typically accomplished through diffusion alone. While diffusion may provide sufficient fluid flow for thin tissues, it is usually insufficient for scaffolds thicker than 200 μm. In order to solve this problem, Stankus et al. employed a perfusion bioreactor to increase fluid flow in the culture (Stankus et al., Microintegrating smooth muscle cells into a biodegradable, elastomeric fiber matrix, *Biomaterials* 27:735 (2006)). However, the bioreactor requires connection to the cell growing chamber and is invasive on the host. There is therefore a need for a minimally invasive method that can both stimulate the cells and promote fluid flow.

Another front of biomedical engineering has been focused on developing devices for efficient and accurate delivery of drugs. One of the goals of this effort has been to create a vehicle that is able to deliver and release compounds at a diseased site in the body. Liposome-based design has been the focus of one line of research; however, it has many shortcomings. More recently, sol-gel technique has been widely used to fabricate porous nanoparticles within a polymer for controlled release of drugs (See generally, Asif et al., Fabrication of nanoparticles within polymeric pores for controlled release of drug. *Pak J Pharm Sci.*, 19:73 (2006)). None of the currently available methods afford the capability to remotely control the release of drugs through a non-invasive mechanism.

Hence, there is a need for a device and a mechanism for delivery of drugs or other materials to target site in vivo where the release of the materials may be controlled remotely by the operation of a magnetic field so as to overcome one or more of the issues and problems identified above.

SUMMARY

This invention provides actuable structures and methods of fabrication and use.

The instrumentalities disclosed here provide a remotely actuable truss structure or scaffold that may house cell growth and tissue formation. Mechanisms for actuating a truss structure with externally generated magnetic fields and methods for fabricating the actuable truss structure are disclosed. Both ordered structures consisting of strut and facet (planar) elements in a regular or partially regular pattern and disordered structures such as random-pore porous or sponge-like structures are considered. The truss may be manufactured by incorporating magnetic particles in a non-magnetic polymer matrix or by curing monomers, such as Nafion, using UV light. Magnetism or other functionalities may be incorporated into the truss concurrent with or subsequent to the formation of the truss structure. If the truss is fabricated using non-magnetic materials, magnetic functionality may be introduced into the truss through ion exchange or other methodologies.

The truss structure may be actuated through application of variety of forces onto the truss structure. For instance, when a magnetic field is applied to the truss structure, magnetic particles incorporated into the truss may displace or rotate under the influence of the magnetic field. Local strain of the truss may be modified by altering the topology and geometry of the truss and the orientation of the magnetization in each strut or facet element or pore wall.

In one embodiment of the idea, the magnetic material in the truss structure may be arranged in spatial patterns of magnetization that lead to beneficial patterns of motion of the truss when it is acted on by a magnetic field. The actuable truss of the present disclosure may contain one or more planar elements or struts which may be magnetized or induced to be magnetized and are arranged in a phased array, such that the orientation of magnetization varies from one element or strut to another. Depending on the orientation of magnetization of individual planar or strut elements, each element may be deflected to a different degree upon application of a magnetic field. In another aspect, the elements may be selectively or sequentially deflected to create a wave of deflections that may pump fluid flow and stimulate cell growth.

In another embodiment, the truss may consist of a random-pore scaffold or sponge-like structure containing magnetic particles whose magnetization is ordered or random.

Magnetic particles of nano or micron scale may be added to the polymers used for making the truss. Several benefits are afforded by the incorporation of these particles. First, cells may adhere and proliferate more readily upon the modified polymer, whereas the unmodified polymer may require surface treatment for cell adherence. Secondly, the magnetically modified polymer may be supplied in liquid form and poured into a mold of desired shape, cast into sheets or formed into thin fibrils of diameter that includes the range of 1 to 10 microns by electrospinning. The fibers formed via electrospinning may be pulled in tension into an approximately collinear array. Cells growing on such collinear fibers tend to extend in the fiber direction. Such cells have favorable shape and alignment for the formation of smooth muscles. Thirdly, the magnetically modified polymers may be deformed by applying a magnetic field, providing a non-contact mechanism for mechanical stimulation of the cells during growth and differentiation. Lastly, the magnetic particles may be acicular in shape and may be caused to align either by flow mechanics or by applying a magnetic field during solidification.

One potential use of the truss structures disclosed here may be in tissue engineering, such as bone healing, or intestine reconstruction, or regeneration of smooth muscle tissue such as heart muscle, blood vessels, sphincter, urethra, or other organs such as liver. Under most circumstances, it may be desirable to use biocompatible materials to construct such a structure. Suitable materials include any magnetically functionalized biocompatible polymer. In one particular aspect of the disclosure, the truss structure may be used in bone healing where the truss may serve as a scaffold for cell growth and differentiation.

A device useful for in vivo delivery of drugs and other materials is disclosed. The device may be fabricated of magnetic materials to create an enclosed space or cavity having trap-door outlets. The outlets may be actuated remotely by application of a magnetic field. This type of device may prove useful for delivering micro-devices or other materials at a desired location according to a specific time frame inside the body. To this end, the entire device is preferably made of materials that are biodegradable so that all materials may be absorbed and purged by the body after use.

BRIEF DESCRIPTION OF THE DRAWINGS

FIG. 4 shows various equations used in the disclosure.

FIG. 6 shows the magnetic properties of $\gamma$-$Fe_2O_3$/PLGA as compared to the magnetic properties of $\gamma$-$Fe_2O_3$ powder.

DETAILED DESCRIPTION

Figure 1A:
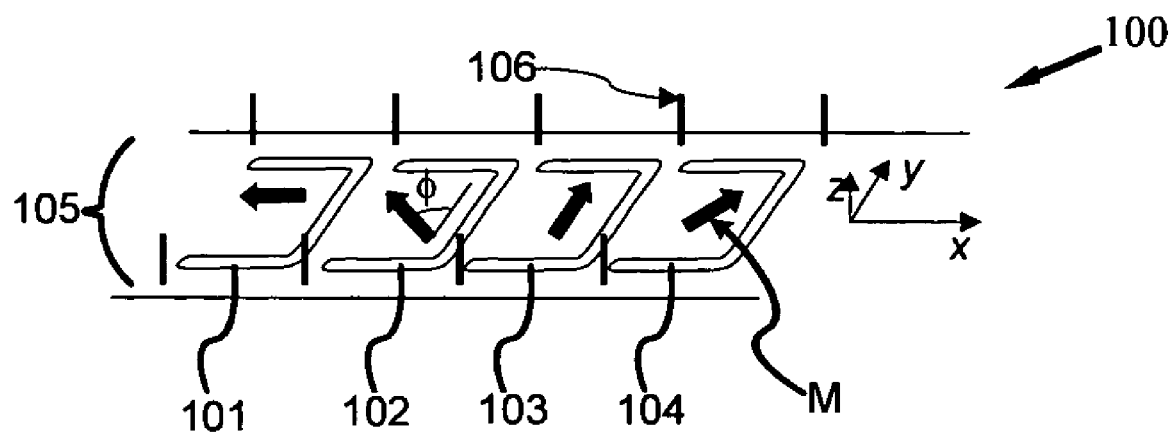
FIG. 1 illustrates the structures of a truss with an array of cantilever plates. (A) A row of magnetized cantilever plates with varying permanent magnetization. (B) Cantilevers embedded in a truss structure and responding to a magnetic field directed along the y-axis.

Before proceeding with the detailed description, it is to be appreciated that the present teaching is by way of example only, not by limitation. The concepts herein are not limited to use or application with a specific system or method for artuable structures and method of fabrication and use. Thus, although the instrumentalities described herein are for the convenience of explanation, shown and described with respect to exemplary embodiments, it will be appreciated that the principles herein may be applied equally in other types of systems and methods involving actuable structures and their methods of fabrication.

Principles of Magnetic Actuation

Magnetic particles, such as $\gamma$-$Fe_2O_3$, may be dispersed in a non-magnetic medium, such as poly(D,L-lactide-co-glycolide) (PLGA). Magnetic actuation of the composite may result in body forces, i.e., forces distributed throughout the bulk of the composite. These forces may arise from the interaction of magnetic particles with the applied magnetic field. Assuming the particle-particle interactions are weak, two systems of forces may exist. First, a particle bearing a magnetic moment, $\mu$, in a magnetic field gradient will be acted on by a body force, F, given by Equation (4) of FIG. 4 (Craik, 1995; Jiles, 1991; see generally Wolfson and Pasachoff, Physics for Scientists and Engineers, 3rd ed. (Addison Wesley, 1999)). The force may tend to displace the material in the direction of the field gradient. It is greatest in magnitude if the moment is aligned with the field gradient. When the particles are paramagnetic, the magnetic moment may be solely induced by the applied field and may tend to align with the field.

Secondly, when the particles are ferromagnetic, the particle may also experience a force moment or torque, T, in an external field, given by Equation (5) of FIG. 4 (See generally Wolfson and Pasachoff, Physics for Scientists and Engineers, 3rd ed. (Addison Wesley, 1999)). The torque may be the greatest if the moment and the field are orthogonal. If the magnetic particles are acicular in shape, the phenomenon of shape anisotropy in the magnetization may favor alignment of the moment with the axis of the particles, rather than with the applied field. The particle may tend to rotate in the applied field, rather than the magnetization rotating within the particle. In this case, Equation (5) implies a distribution of moments throughout the composite, which may tend to bend the material. This effect may add an additional level of control over the characteristics of the motion induced in a scaffold.

Magnetic Modification of Polymers for Actuation

Various methods may be used for incorporating magnetic particles in polymers.

Particles of interest include those in ferromagnetic, paramagnetic, ferrimagnetic, antiferromagnetic, superparamagnetic or other magnetic states. Particles of sizes ranging from single atoms to diameters of 1 mm can be of interest. The particles may also contain non-magnetic surface coating or shell to prevent agglomeration. The shapes of the particles might be spherical, acicular, plate-like, or irregular.

The use of acicular particles may be desirable, because a high particle aspect ratio may create a shape anisotropy effect, by which magnetization tends to align with the particle axis, rather than with the applied field. This is useful for actuation, since a mechanical torque is exerted on a magnetic particle only when the field and the particle's magnetization are not aligned. In one approach, magnetic nanoparticles may be embedded in polymer matrix with an aspect ratio of 10:1, which provides a desirable shape anisotropy effect.

In another embodiment, ferromagnetic particles, including but not restricted to particles that are larger than 0.1 µm, may be used. Larger particles also tend to have higher magnetization per unit particle volume, because they are less affected by surface dead layers, a phenomenon in which magnetization is diminished by weak exchange between atoms on the surface of a particle. For these ferromagnetic particles, shape may become a secondary consideration, and their magnetization may be orientated by applying a poling field, regardless of whether the particles are spherical or not. A subsequently applied, weaker field acting at a different angle may then exert a torque.

Particles of all shapes and types of magnetic ordering may also be actuated by an applied magnetic field that possesses a spatial gradient, resulting in a body force acting on the particle as well as a possible torque.

Ferromagnetic particles, such as 200 nm $Fe_3O_4$ particles, and other particles may be incorporated in polymers by mixing, casting into thin sheets, and curing, using methods familiar to those in the magnetic tape industry (See e.g., Ramprasad et al., 2004). This method may be especially suitable for simple fabrication of thin films of ferromagnetic polymer composites, from which truss structures with plate members, rather than strut, may be conveniently fabricated. Additionally, magnetic particles may be incorporated into polymer matrix and formed into fibers via electrostatic spinning.

Particles of widely selectable sizes, from ~5 nm to 1 µm or more, may also be incorporated into the polymers using novel ion-exchange methods as described by Giannelis and Mehrotra 1991a and 1991b, Mehrotra et al. 1991, Mehrotra and Giannelis, 1992, Ziolo et al. 1992, Vassiliou et al. 1993, Mehrotra 2001). A host polymer is used with ion exchange sites and nanoclusters, which act as templates for in situ synthesis of functional foreign species (see U.S. patent application Ser. No. 10/837,552 by Mehrotra et al.). The size and shape of the nanoparticles may depend on the nanocluster distribution in the host, which may be controlled by mechanical stretching. Nanoparticles may also be grown in situ to much larger sizes (e.g., 1 µm), depending on the desired functionality. Particle volume fractions of up to 40% may be achieved by iterating the ion exchange and precipitation steps. Suitable polymers may include, for example, perfluorosulphonic acid, polyethylene oxide, and co-polymer blends. Of these, at least perfluorosulphonic acid membranes have been shown to be biocompatible as implantable sensors (Turner et al., 1991, Turner and Sherwood 1993). Many materials may be incorporated, including iron oxide nanoparticle composites with magnetization 10-30 emu/g and composites of metallic nanoparticles capped with a protective coating and magnetization 100-300 emu/g. Suitable materials include, for example, $Fe_2O_3$, $Fe_3O_4$, $MnFe_2O_4$, $CoFe_2O_4$, $NiFe_2O_4$, Ni—Fe alloys, Mn, Co, or Fe with inert coatings. Magnetic materials suitable for this disclosure preferably present low corrosion rates and are nonimmunogenic and biocompatible. There have been reports suggesting that materials such as $\gamma\text{-}Fe_2O_3$ may satisfy most of these criteria (Rehman and Landman, 2002; Weissleder et al., 1989).

In assessing the overall performance of the scaffold, truss mechanics may imply a preferred range of larger particle sizes, in order to achieve a higher magnetic force development. However, biological applications, especially issues of biocompatibility, may call for nanoscale or intermediate sized particles. The methods disclosed herein are applicable for particles of a wide range of sizes.

Fabrication of the Truss Structures

One way of forming the actuable structures 100 of FIGS. 1 and 2 is to first fabricate thin sheets of magnetically modified polymer (such as polyethylene oxide, poly(lactic-co-glycolic) acid, polycaprolactone, polyglycolic acid, polylactic acid, polyethylene glycol etc.). The thin sheets may be cut, for example, by etching. The cut sheets may then be laid in a stack, and welded together by running a laser along intended joint lines. The joined sheets may be opened out by internal gas pressure or mechanical forming. This general technique may be used to fabricate honeycomb cores in structural sandwiches which may be used in, for example, aircraft wings. FIG. 3D depicts a honeycomb structure 350, with plates cut out to form apertures or to create slender struts. Since the laser beam may be focused optically, structures with scales as small as 10 µm may be feasible, which is beneath the range of sizes preferred for cell scaffolds. Much larger structures with complicated topology and geometry may also be built up. Laser welding of a thermoplastic polymer may also be used to join truss structures to themselves or other trusses, for instance, to form closed toroids for developing a sphincter function. It is also desirable to create apertures and thinnings at joints to increase the truss compliance.

An alternative approach for fabricating trusses is to first create a truss consisting of unmagnetized polymer via freeform manufacturing methods. Magnetic function may then be incorporated without deleterious alteration of the geometry, by ion exchange. Free-form fabrication is now available for making complex shapes using well-standardized apparatus (See e.g., Schroeder 1998). At least two approaches may be taken. The first is called stereo-lithography which involves selective curing of a polymer precursor with a scanning laser or projected image. Briefly, an uncured liquid polymer is introduced in a thin layer within the work area. An ultra-violet laser, which may be robotically controlled and linked to a Computer-Assisted Design (CAD) program in which the desired component shape has been stored, scans the work area and cures (or solidifies) the polymer that lies within the boundaries of a prescribed domain. The domain corresponds to the shape of a slice of the component. The body may be built up slice by slice. The second approach is called robotic ink-jet writing using shape-holding, viscous colloidal inks (Smay et al., 2002). In this method, the desired shape may be produced by robotically controlled deposition of extrusions of viscous ink from a fine nozzle.

As compared to the robotic ink-jet writing, stereo-lithography is better developed and is capable of creating more general shapes, including high-aspect ratio plates or struts that are neither orthogonal nor confined to planar arrangements. Components with arbitrary connectivity may be created via stereo-lithography, which may be an important attribute for the varied truss structures, especially those to be used for bio-actuation. Polymers that may be cured from a liquid form by UV radiation and are therefore well-suited for free-form fabrication may include biocompatible polymers such as Nafion. Using focused laser light for curing, free-form fabrication can create structural features as small as 0.01-0.1 mm.

Actuable Porous Scaffolds

A lattice of random pores can serve as a scaffold. Addition of magnetic material to the porous scaffold or spongiform material enables actuation under applied magnetic fields. Random-pore scaffolds may be formed via leaching of a porogen/magnetically modified polymer (ex. sugar/$\gamma$-$Fe_2O_3$/PLGA) mixture. Several approaches for the formation of porous scaffolds exist, including salt leaching, phase separation, gas blowing and ice. The pore size, pore volume fraction, and pore distribution and arrangement may be determined by the processing conditions. Cuboidal and disk-shaped specimens may be fabricated by using molds of desired size and shape.

Figure 5:
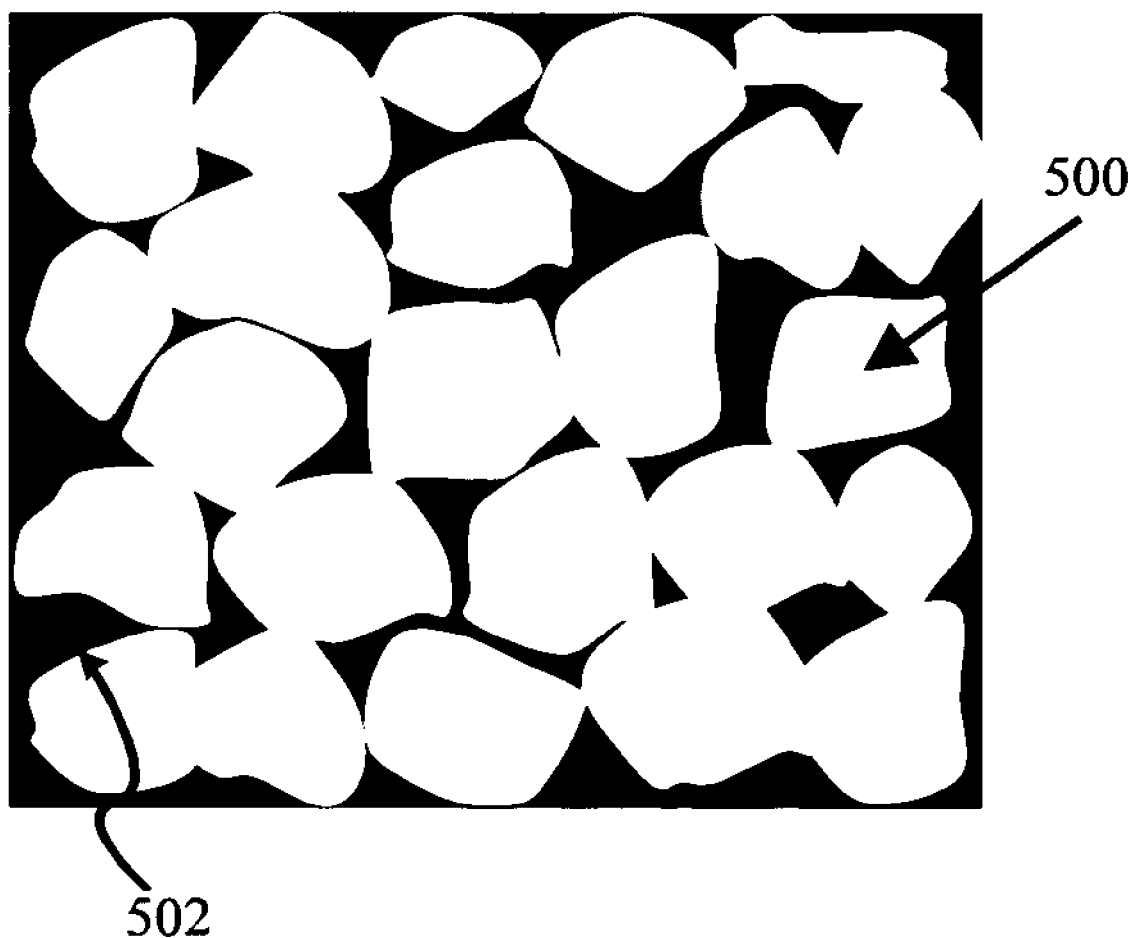
FIG. 5 shows the surface of a typical random-pore scaffold.

The morphology of the magnetically modified porous scaffolds may be characterized by optical microscopy and scanning electron microscopy (SEM). FIG. 5 shows a line drawing of a typical porous scaffold surface with a distribution of pores 500 in the scaffold material 502. The distribution of magnetic particles through the random pore scaffold may be analyzed. The magnetic properties, including any permanent magnetization and hysteresis loop of the material, may be determined using a Superconducting Quantum Interference Device (SQUID). FIG. 6 shows the result of a typical analysis of the magnetic properties of $\gamma$-$Fe_2O_3$/PLGA as compared to the magnetic properties of $\gamma$-$Fe_2O_3$ powder.

Achieving Circumferential Contraction and Peristaltic Motion

Figures 7A, 7B, 7C:
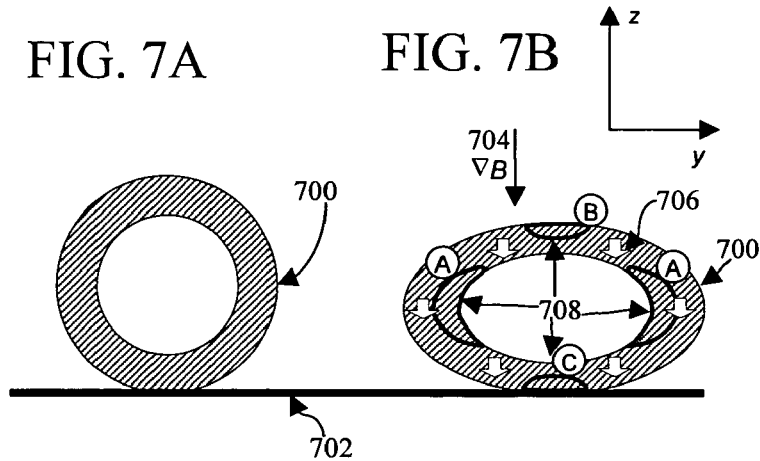
FIG. 7 is a schematic of a tube or toroid made of magnetically functionalized material in a paramagnetic state in the absence (A) or presence (B and C) of an actuating magnetic field gradient with deformation restrained by a flat plate (B) or a curved plate (C).

Sheets of magnetically modified polymers and magnetically modified random-pore scaffolds may be formed into tubes or toroids by fabricating in Teflon molds. Cross sections of such a tube 700 is shown in FIGS. 7A~7C Actuation of the tubes or toroids 700 may be studied by applying magnetic fields, with deformation restrained by a flat plate 702 (see FIGS. 7A, 7B) or a curved plate 703 (see FIG. 7C). The constraining plate 702 or 703 may restrict induced strains to desirable deformation patterns. For in vivo application, an equivalent constraint may be supplied by the surrounding hard tissues or muscle walls. The geometrical details of the tubes or toroids 700, and constraint plates 702 may be optimized by a combination of mechanical testing and deformation modeling to create circumferential strain patterns similar to the biological strains that occur during peristaltic motion and sphincter contraction for example. For peristaltic motion, it is preferred that the circumferential contraction propagates as a pulse along a tube.

Figure 8:
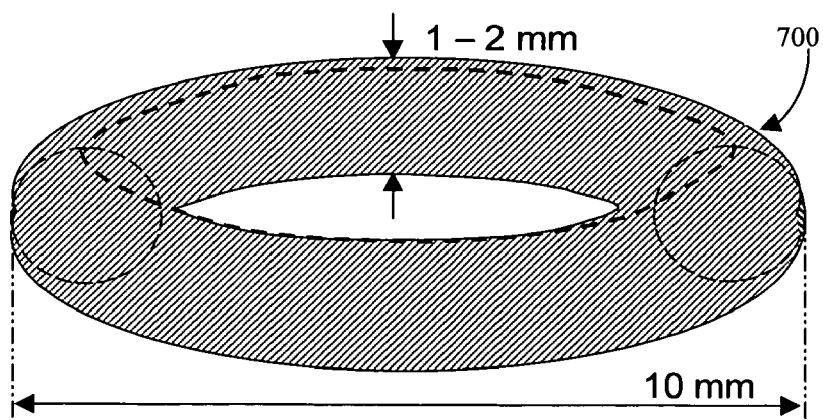
FIG. 8 shows a toroidal scaffold with same outer diameter and wall thickness as a tubular scaffold.

Referring now to FIG. 8, in one embodiment, the outer diameter of the tubes or toroids may be approximately 10 mm and the wall thickness of the tube or small diameter of the toroid may be approximately 1-2 mm. Since large deformations may be envisaged, both membrane and shear components of strain may be substantial, depending on the nature of the loading boundary conditions. Under certain circumstances, large membrane strains may be advantageous for stimulating cells into aligned growth.

Figure 9:
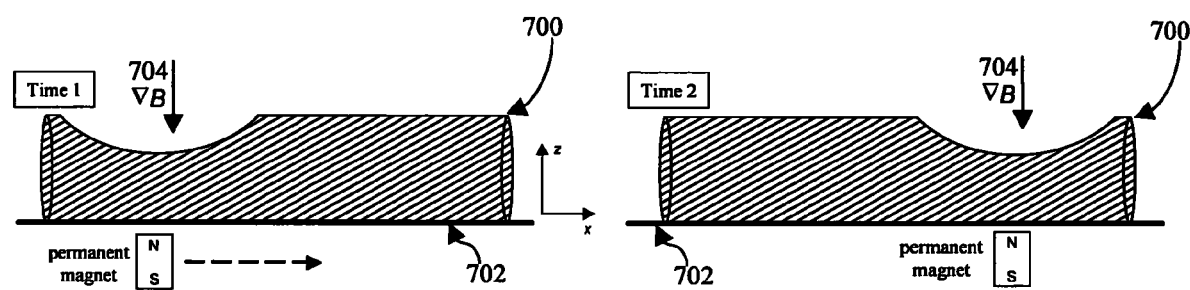
FIG. 9 illustrates a contraction moving along a tube as a pulse driven by a moving magnet.

FIG. 9 illustrates, by way of example, methods of deforming a tube, viewed on a section (the y-z plane) normal to the tube's axis of revolution. In these diagrams, the wall thickness may be exaggerated for clarity in sketching features of the induced strains. The tube or toroid 700 may be subjected to a magnetic field gradient 704, $\nabla B$, such that body forces 706 arise throughout the material of the tube in the downward direction as indicated in FIG. 7B. The tube may be constrained by a flat plate 702. Consideration of shear force and bending moment equilibrium around the section reveals that zones of compressive strain in the circumferential direction 708 arise primarily at four locations, as indicated by capital letters A, B and C in FIG. 7B. Adjacent to these may be compensating tensile zones. If the overall deformation is large enough, plastic hinges may form at points A and further deformation may be concentrated there.

An alternative constraint geometry is a curved plate such as the stiff cylindrical shell 703 shown in FIG. 7C. Since the cylindrical constraint 703 encloses the tube or toroid 700, it may be perforated so as not to inhibit fluid and nutrient flow. A very open stiff mesh may be sufficient for the purpose of constraint. The cylindrical constraint may be effective regardless of the direction of the applied magnetic field gradient 704. The zones of compressive strain in the circumferential direction 708 arise primarily at four locations, as indicated by capital letters A, B and C in FIG. 7C. A zone of constraining contact 712 exists between the tube or toroid 700 and the curved constraint 703 as shown in FIG. 7C. If the field gradient 704, $\nabla B$, is continuously rotated, a cycle may be established in which most of the material in the tube may experience for a significant accumulated time period a state of circumferential strain.

The peristaltic motion created in the tubes may be optimized by passing a permanent magnet along the length of a tubular scaffold. FIG. 9 shows a pattern of deformation that is moving along the length of the tube as a pulse. The pulse may be driven by the field gradient associated with the moving permanent magnet. The deformation may be governed by several rate dependent processes, including, for example, the speed of the magnet, the viscoelastic response of the scaffold, and, if the tube is immersed in a fluid, the dynamics of the fluid. The deformation of the scaffold and the flow of fluid in and out of the scaffold may depend on the pore size of the scaffold and the pore volume fraction.

The deformation of a toroid on a bisecting plane normal to its axis may look similar to the patterns described in FIG. 7A~7C. Design considerations for the tubes discussed above may apply to the design of a toroid structure with some modifications.

The function of magnetically actuated trusses may depend on the truss configuration, such as topology and geometry, and the distribution of magnetization among the truss members. It is also recognized that the order of magnitude estimates of forces and displacements in simple trusses may demonstrate the principal concepts and the feasible magnitudes of actuation.

Actuable Trusses for Soft Tissue Stimulation

Figure 1B:
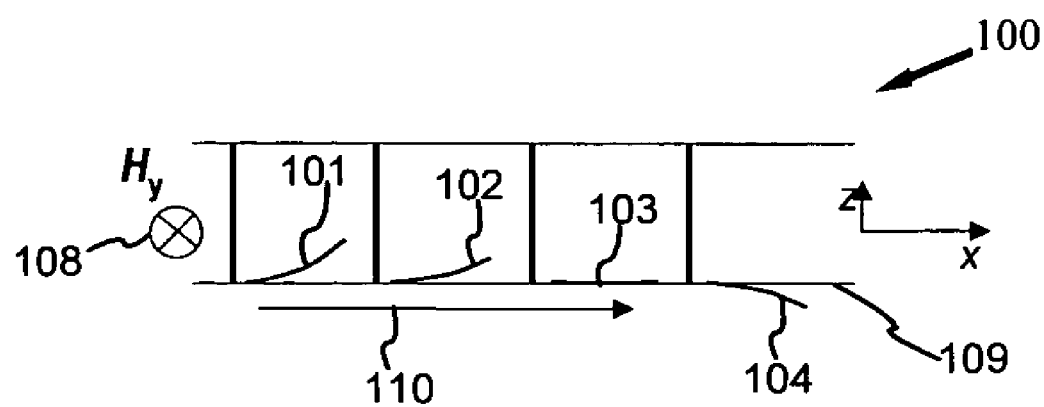

FIGS. 1A and 1B illustrate a portion of actuable truss structure 100 in accordance with at least one embodiment. The truss structure 100 of the present disclosure may contain multiple planar or strut elements of which planar elements 101, 102, 103 and 104 are shown for purpose of illustration. These planar elements 101, 102, 103 and 104 may also be referred to as cantilever plates. The cantilever plates may be arranged as an array 105. The array 105 may be connected with other arrays (or layers) of cantilevers via a structure such as a strut 106, as shown in FIG. 1A. The cantilevers may be fabricated of polymer carrying a dispersion of magnetic material. In one preferred embodiment, the magnetic material is iron oxide. The magnetization of these magnetic materials is designated M, and the orientation of the magnetization, as indicated by the thick solid arrows in FIG. 1A, may be arranged to vary along the array of cantilever plates by applying a strong localized poling field. In one aspect, the localized poling field may be created using a magnetic write head.

A uniform magnetic field 108, with a magnitude of H, may be subsequently applied to the structure 100. H is preferably of a magnitude that is insufficient to re-orient the magnetization M, as depicted in FIG. 1A. Depending on the orientation of the magnetic moment in each cantilever and the direction of the uniform magnetic field 108, a torque proportional to MHcos$\phi$, where $\phi$ is the angle as defined in FIG. 1A, acts on each cantilever. The application of this torque may result in the sinusoidally varying pattern of deflections shown in FIG. 1B (See also Liu et al. (1999) for a similar concept with different materials for aerodynamic flow control). When H 108 is acting along the y-axis, thus the designation $H_y$, as shown in FIG. 1B, cantilever 101 is deflected the most, while cantilever 103 is not deflected. If the field 108 is now rotated to be aligned with the x-axis, the deflections may change such that cantilever 103 is now deflected most and cantilever 101 is not deflected. Thus, a rotating field 108 creates a wave-like variation of deflections. Since a deflected cantilever displaces fluid from the volume it sweeps, a phased array of cantilevers generates a pumping effect.

In another embodiment, the array of cantilevers 105 may be embedded in a truss and is thus opposed by a fixed impermeable or semi-permeable plate 109, as shown in FIG. 1B. Under these circumstances, a fluid pressure gradient 110 is likely to form in the x-direction. Fluid flow or pressure may create shear loading on cells that adhere to either the cantilevers or the other structural members across which the fluid passes. Fluid flow also helps transport of nutrients and wastes.

Figure 2A:
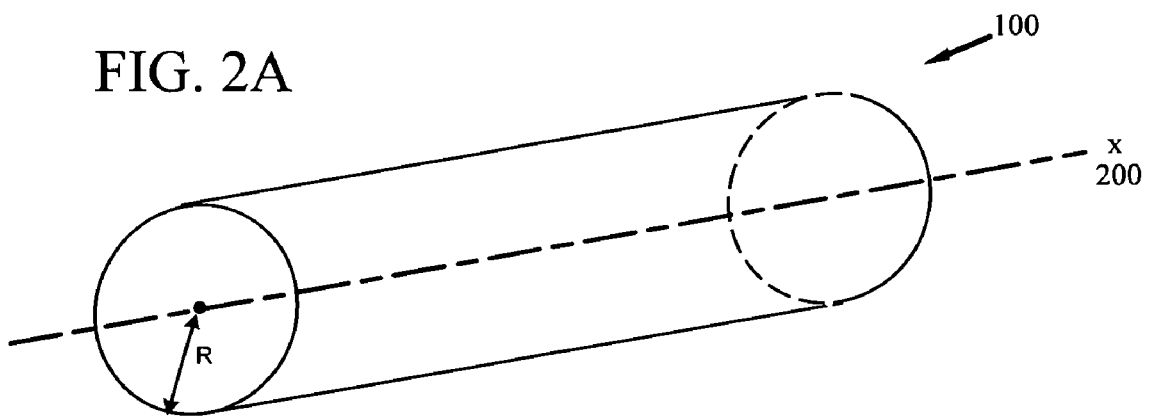
FIG. 2 are a few representative structures whose walls or body might be formed with either ordered or disordered truss material showing the body portion as a cylinder (A), a triangle (B) or a rectangle (C). x is the longitudinal axis and R is the distance of disposition from the periphery of the body portion to the x-axis.
Figure 2B:
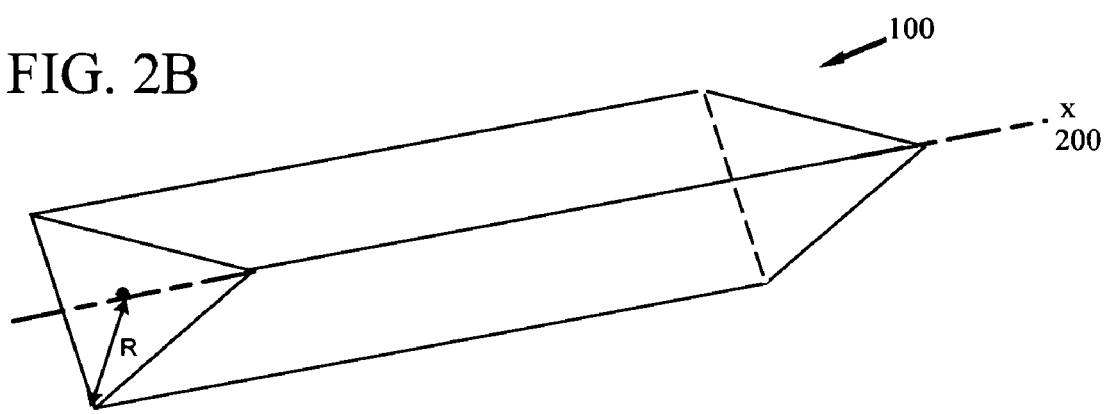
Figure 2C:
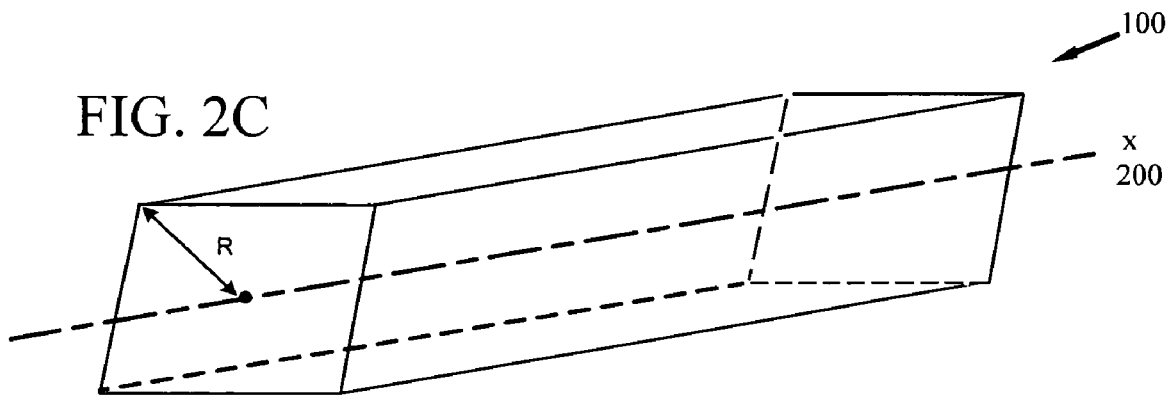

In another embodiment, the structure 100 may contain a body portion having a longitudinal axis, such as axis x 200 in FIGS. 2A~2C. The body portion may contain one or more chambers connecting to one another. The body portion may be radially disposed at a pre-selected distance, R, away from the x-axis. Different cross sections perpendicular to the x-axis through the body portion may yield different planar shapes, which may include triangle, quadrangle, or other polygons with N sides. As N increases to approach infinity, the cross sectional planar shape becomes a circle or an oval. Accordingly, the value of R may be uniform or may be variable depending on the shape of the body portion at the particular cross section. The body section may extend along the x-axis at a direction that is substantially parallel to the x-axis.

Figure 3A:
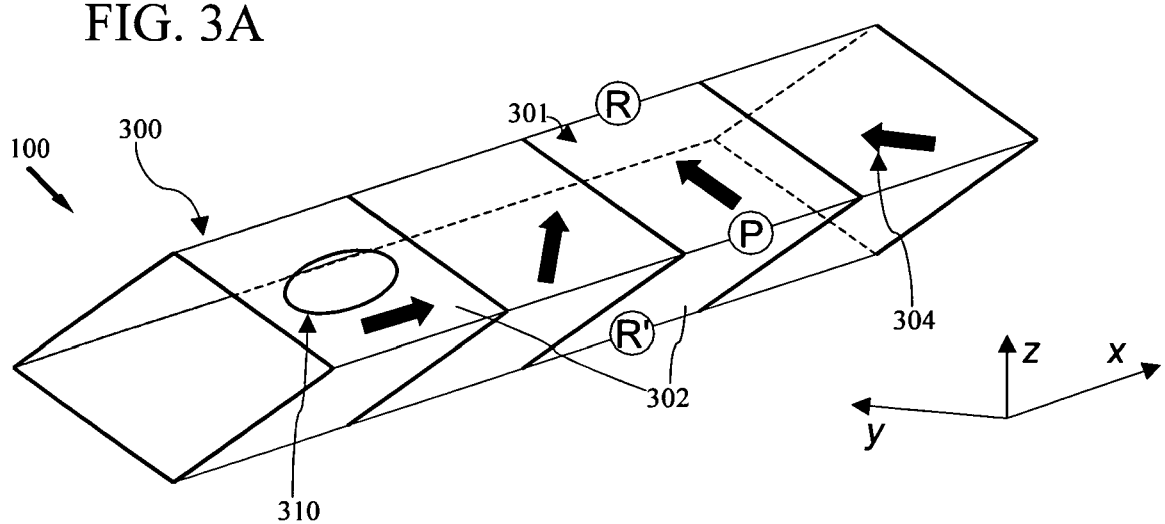
FIG. 3 illustrates different ordered truss structures and their deformation upon actuation. (A) Tube-like truss structure. (B) Deformation of segment a under applied field acting in x-direction. (C) Pumping deformation of tube in (A) due to sinusoidal variation in orientation of magnetization. (D) Accordion-like truss structure.

In one aspect, the structure may be a tube-like structure 300 made up of different segments (or chambers), as shown in FIG. 3A. In one particular aspect, the segments may be prismatic shell segments as shown in FIG. 3A. The prismatic shell segments may be physically joined and thus hermetic. One of the segments 301 is shown and analyzed in FIGS. 3A, 3B and 3C for purpose of illustration. The plate-like sides 302 of the shells may bear ferromagnetic material, whose magnetic orientation 304 varies from segment to segment, as indicated by solid black arrows in FIG. 3A.

A magnetic field 305, with a magnitude of $H_x$, may be applied along the x-axis, the same as the axis of the prismatic shells. By way of example, segment 301 is likely to contract in the z direction and expand in the y direction, as shown in the cross section in FIG. 3B. Other segments may distort less, because their magnetization 304 may not be orthogonal to the applied field 305 (M×H reduced), as shown in FIG. 3C. Thus, depending on the orientation of magnetization 304 and the direction of the applied field 305, the different chambers of the truss structure may be deformed or distorted selectively or sequentially in an applied magnetic field. In one embodiment, as illustrated in FIG. 3A, the row of prismatic shell segments may bear magnetic moments of rotating orientation and may develop a wave-like motion of contraction and relaxation when the field 305 is rotated. This phased movement of the segments may cause the fluid to be pumped along the x-axis, in a direction indicated by the open arrow 306 in FIG. 3C.

The distortion may also generate strains in the structure itself, which may result in a distorted channel-like structure 308 as shown in FIG. 3C. The major components of the strains in the structure 308 are strains $\epsilon_y$ and $\epsilon_z$, which usually have opposite signs in a given segment (The subscript x, y or z denotes the direction of strain in an xyz three-dimensional coordinate system.). Thus, in the structure 308, the principal strains likely arise in directions normal to that of the primary fluid flow 306. In another aspect, apertures 310 may be created on the plate-like sides 302 to allow for the ingress and egress of materials and propitiation of angiogenesis, nerves and other tissue functionalities.

In yet another embodiment, the truss may be an accordion-like structure 350 containing plates 351 with varying orientation of magnetization 353 as shown in FIG. 3D. The plates 351 are preferably joined by struts 355. A wave-like distortion may be created under a rotating applied field which may result in fluid flow 358 in the x-direction and strains $\epsilon_x$ and $\epsilon_z$. Thus one of the principal strains, $\epsilon_x$, acts in the same direction as that of the primary fluid flow 358. Apertures 310 may be created on the plates 351 to allow for fluid ingress and egress and propitiation of angiogenesis, nerves and other tissue functionalities.

The scale of the truss structures is a design variable, whose optimal values vary according to the cell and tissue types and other parameters of the particular application. The range of dimensions, generally in the range of 0.1-1 mm, may be most appropriate for the plates or struts in trusses such as those depicted in FIGS. 3C and 3D. This range allows easy injection of cells and offers adequate apertures for nutrient transport into the truss. Nutrient may flow readily along the x-axis in FIG. 3C and along the x and y-axes in FIG. 3D. Flow in other directions and space for angiogenesis, innervation, and other tissue functionalities may also be provided by leaving apertures, such as aperture 310 in the truss 300 as shown in FIG. 3A.

To use the disclosed structure for cell culture, cells may be seeded in the truss structure with an initial low density. Individual cells may not touch each other at this stage, but they may adhere to individual members of the truss (plates and struts). Actuation of the truss may stimulate the cells by viscous drag as fluid is pumped through the structure. As the cells proliferate, they fill more of the internal volume of the truss, until aggregates of connected cells reach from one member (plate or strut) of the truss to another. At this stage, direct mechanical loading of the cells becomes possible, as the plates and struts experience relative motion during actuation. The cell loading is preferably ordered because the truss is ordered. An experimental question is the optimal combination of orientations of fluid flow (shear traction on cells) and mechanical strain. Because a truss may be manufactured as a tube-like (FIG. 3A) or an accordion-like (FIG. 3D) structure, or any of the numerous variants therefrom, depending on the structure and material of the trusses used, the shear tractions and mechanical strain may be chosen to be parallel or orthogonal to each other.

Trusses formed from flexible polymers in the geometry indicated by FIG. 1, 2, 3 or 5 may be bent into curved paths over distances that are long compared to the unit segment (repeating unit) size. For example, tubes and channel structures could be bent head-to-tail into closed loops, forming scaffolds with the general structure of sphincter or intestine. The mechanics of actuation and the underlying principles are the same as those used for the linear structures. However, when closed loops are formed, one route for ingress and egress of fluids is lost. Fluid exchange between the truss and the surrounding environment may occur, for example, via apertures 310 in plate members 302 as shown in FIG. 3A. Proper size of apertures or pores may be determined as a compromise between the need to facilitate fluid flow in and out of the truss, and the need to maintain sufficient constraint on flow such that pressure gradients still drive fluid along tubes and channels within the truss.

In one aspect of this disclosure, large strain deformation may be achieved by bending of the plates or struts of a truss design, such as those of FIG. 3, without developing any membrane strain in the same. A compliant truss that deforms in this way is desirable, because it may be less resistant to the forces created by the actuating field, allowing those forces to act on cells or fluids residing within the truss.

Figure 3B:
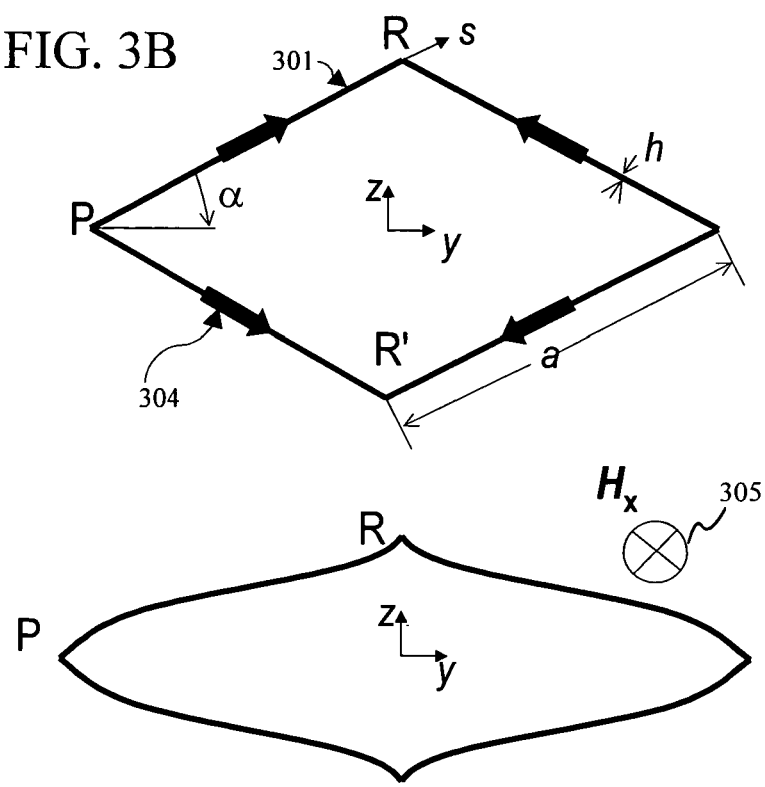
Figure 3C:
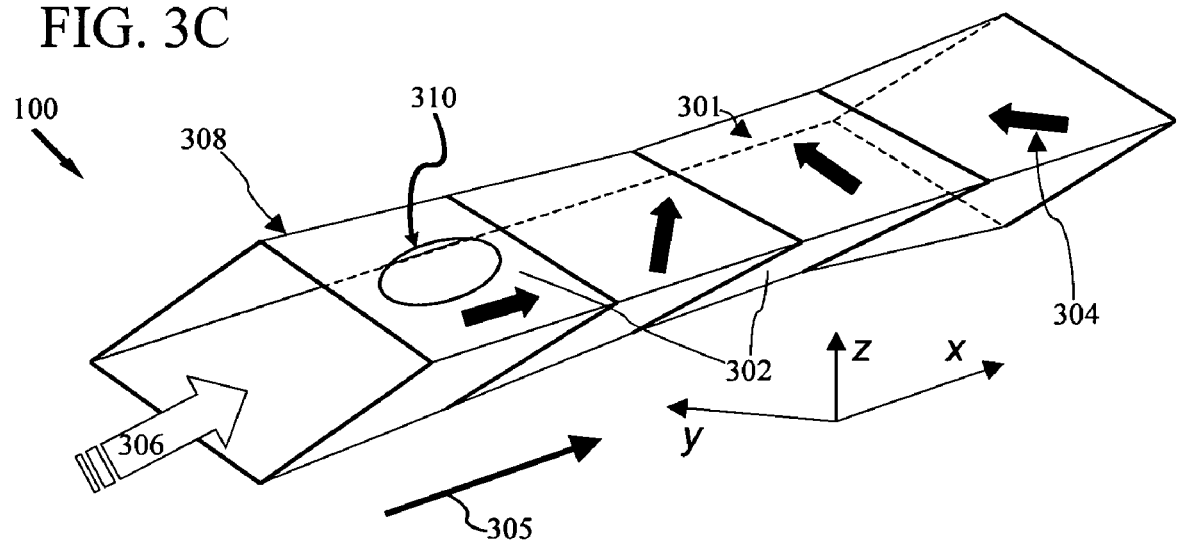
Figure 3D:
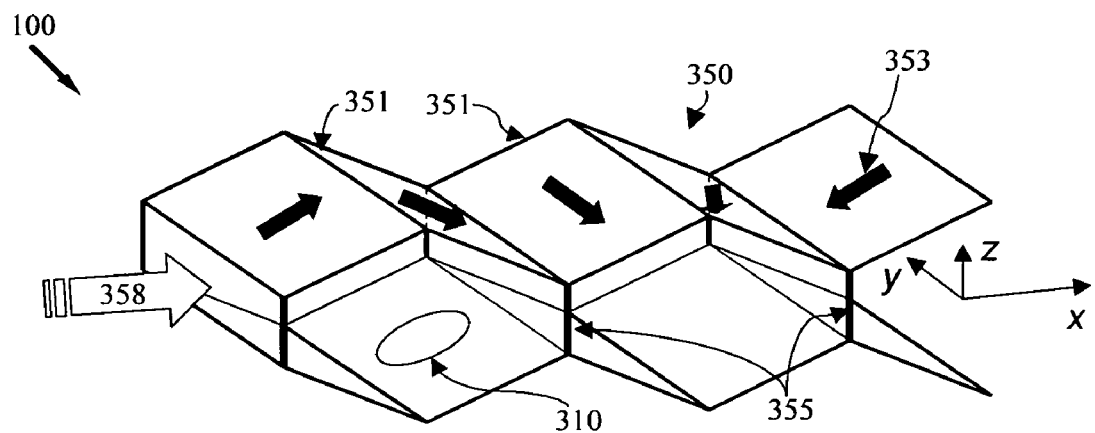

For purpose of illustration, some representative numbers may be deduced from analysis of the unit of four plates depicted in cross-section in FIG. 3B. Suppose the plates each contain magnetic nanoparticles with magnetic moment/unit volume, M, and a magnetic field 305 with magnitude $H_x$, that acts in the x-direction as shown in FIG. 3B. The field 305 generates a torque on the magnetic moments, which tends to bend the plates (See Jiles, 1991). According to the Euler-Bernoulli beam theory (Timoshenko 1930), which is accurate for thin plates or struts, the induced macroscopic strains (defined as the average displacements over the truss) may be calculated according to Equation (1) of FIG. 4, where $\mu_0$ is the permeability of free space, E is the Young's modulus of the plate material, a, h, and $\alpha$ are as defined in FIG. 3B, and $\eta$ is the dynamic viscosity of the fluid. The effective macroscopic Young's modulus of the truss in the z-direction is provided by Equation (2) of FIG. 4.

The deformation caused by the magnetic actuation is identical in shape, in the limit of Euler-Bernoulli beam theory, to that caused by an external mechanical load, e.g., line forces $F_z$ per unit length acting in the z-direction at each vertex. Therefore, the macroscopic work done in deforming the truss under magnetic actuation exerted by field $H_x$ in the x-direction is $W_t = E_z \epsilon_z^2 / 2$, with $\epsilon_z$ and $E_z$ given by Equations (1) and (2).

These results are calculated based on the assumption that the edges of each plate are built into the nodes (or vertices) of the truss, or in other words, zero rotation of plates at the vertices exists. In practice, however, selective thinning of plates at nodes may permit some rotation which may lead to increase in strains. In turn, the truss stiffness may decrease, and the work needed to deform the truss may decrease as well. In the limit of zero resistance to rotation at the nodes, such as under the condition of smoothly pinned joints, $\epsilon_z$ and $\epsilon_x$ both approach $\infty$ and thus $W_t$ also approaches $\infty$. Under these circumstances, the truss becomes a "mechanism" as used in the jargon of truss mechanics (See Maxwell, 1864 and Calladine, 1978).

For the pin-jointed truss (or "mechanism"), the mechanical line forces, $F_x$ and $F_z$, applied per unit length externally at the nodes of type P and R (FIG. 3B) that would be required to cancel the magnetic actuation are provided by Equation (3) of FIG. 4. These forces may also be regarded as the maximum forces the truss may impose on material trapped inside the tube-like structure of FIG. 3A, or with minor changes of geometry, the channel of FIG. 3C. The forces, $F_x$ and $F_z$, are independent of the plate length a (FIG. 3B). In the event that the truss is altered in scale at fixed aspect ratio, h/a, the forces per unit length vary linearly with the length scale, while the number of nodes per unit length in the y-direction increases at the same rate, such that the spatially-averaged stress developed remains constant. Self-similar scaling of the truss may therefore be taken over a wide range while maintaining the actuation effects.

For purpose of illustration, the orders of magnitude for responses of interest may be calculated by assuming the following values: $H_x$=106 A/m (large laboratory magnet); $\alpha = \pi/4$; M=$1.2 \times 10^5$ A/m (typical of ferromagnetic particle dispersions); h=0.1 mm; E=1 GPa; $\mu_0 = 4\pi \times 10^{-7}$ $NA^{-2}$. For these data, the forces per unit length, $F_x$ and $F_z$, generated by a pin-jointed truss both take the value 30 mN/mm ($10^{-2}$ N/mm). If, for example, a pair of line forces of this magnitude is to act through nodes R and R' (FIG. 3B) on an entrapped mass of cells of area 1 $mm^2$ and the modulus of the cells is $E_c$=1000 Pa (See Zahalek et al. 1990), a strain in the order of magnitude of 300% may be generated. Cell stiffness may vary widely depending on the gauge of the test, and some cells may exhibit viscosity at moderate rates of loading. Therefore, large strains may be generated in the elastic regime as shown here and the effective modulus may be used as a rough indicator of cell behavior.

For a truss that is not pin-jointed but has rigid nodes, the stiffness of the truss itself may limit deformation and strains imposed on the entrapped soft tissue may be reduced. With the same set of assumed values as above and with plate aspect ratio a/h=10, the strain induced in the absence of entrapped tissue is ~1.5%, which is significantly smaller than the strain pin-jointed condition. Methods to increase this value include, for example, thinning the plates and struts near nodes of the truss to promote rotation.

In another embodiment, ordered truss structures of the type described in this section may be actuated by a magnetic field possessing a spatial gradient dH/dx in its magnitude. Such a gradient field may cause magnetic particles in the actuable truss structure to displace as well as rotate, making possible further attainable patterns of strain in the truss structure.

The Role of Mechanical Stimulation on Smooth Muscle Cell Behavior

Studies have shown that mechanical strain regulates smooth muscle extracellular matrix (ECM) metabolism and increases the synthesis of collagen, elastin (Kim and Mooney, 2000) and proteoglycan (Lee et al., 2001). Conflicting results have been reported in the response of smooth muscle cells (SMCs) to cyclic strain with respect to vascular bed derivation and the species under study. This discrepancy in response has been partially attributed to the use of different strain regimes (Mills et al., 1997). Vascular SMCs have been shown to generate a mitogenic response to mechanical strain through the induction of platelet-derived growth factor (PDGF), which is regulated by specific ECM interactions (Yang et al., 2003).

Mechanical stimulation of stomach SMCs in collagen gels has been shown to convert the SMCs into a morphologically differentiated phenotype. However, mechanical stimulation alone is not sufficient to maintain the immunocytochemically differentiated phenotype (Oishi et al., 2000). Cyclic mechanical strain has been shown to have a dual effect on vascular SMC phenotypes. First, it may augment SMC proliferation in serum-activated cultures; secondly, it may increase the expression of h-caldesmon, considered a marker of a differentiated smooth muscle cell state. The increase in h-caldesmon expression has been shown to be reversible with the removal of mechanical stimulation (Birukov et al., 1995).

Myometrial SMCs from rats have been reported to respond to mechanical stretch with a strength- and matrix-dependent increase in c-fos messenger RNA levels. The time lag between the initial stimulus and the cumulative increase of c-fos messenger RNA suggests a complex regulation from mechanical stimulation and reception to c-fos gene expression (Shynlova et al., 2002). The contractile mechanism in vascular SMCs may be activated by several different signal transduction pathways. All of these pathways first lead to an increase in intracellular $Ca^{2+}$ concentration $[Ca^{2+}]_i$ (Yang et al., 2003).

Magnetically Actuable Devices for Delivery of Materials

Figure 10:
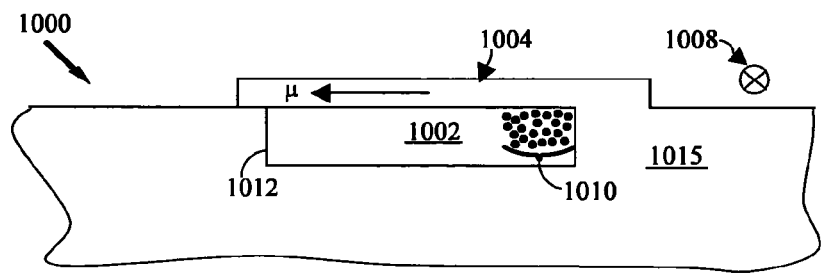
FIG. 10 shows a magnetically actuable device containing an enclosed space (or cavity) with one or more trap-door outlet.

In one embodiment, a magnetically actuable device 1000 may be fabricated such that it contains an enclosed space (or cavity) 1002 with one or more trap-door outlet 1004 as illustrated in FIG. 10. The trap-door outlet 1004 may be actuated by application of a magnetic field 1008. In one particular aspect of this disclosure, the enclosed space may contain materials 1010 such as chemical or biological agents. For example, the cavity may contain compositions for treating diseases, compositions for labeling certain cells or tissues, or even living cells of human or non-human origins. The materials inside the cavity may be in gas, liquid, or solid phase including powder form. In another aspect, the materials contained in the cavity may include micro-devices only to be released after being transported to a desired body site. Examples of such micro-device may include camera, laser knife or other medical devices capable of performing a medical therapy or procedure.

The materials 1010 including micro-devices contained in the cavity 1002 may be released from the cavity when the trap-door 1004 is open or otherwise becomes permeable. The cavity 1002 may be constructed using the disclosed tubular or toroidal structures such that peristaltic movements may be generated on the cavity wall 1012 upon the application of the actuating field 1008. These peristaltic movements may help pump the materials 1010 out of the cavity 1002. The trap-door 1004 may be a cantilever containing magnetic materials. Actuation by the magnetic field 1008 may result in movement of the cantilever which may open the trap-door 1004. In another aspect, actuation may cause permeability change of the trap-door 1004 and consequently release of the materials 1010 in the cavity. The content of the cavity may be released in whole or it may be released graduately in small portions each time the device 1000 is actuated.

The device 1000 may be fabricated in small scale to suit its potential use inside the body of a human being or an animal. The device 1000 may be implanted into the body of the host, or alternatively, it may be injected into the blood stream of the host. Where it is desirable for the device to be mobile inside the host body, it is preferable that the device be guided to its target destination. Methods to guide the device may include physical or biological means. Physical means may use magnetic or radio frequency signals to guide the movement of the device inside the body of an animal or a human. Biological guidance may include, for example, the use of antibodies to target the device to a desired destination. It is also desirable to use materials that have low corrosion rates and are nonimmunogenic and biocompatible. Preferably, the entire device 1000 may be made of biodegradable materials 1015 such that the materials may be absorbed and purged by the body after use. In one aspect, the biodegradability of the device may also be controlled remotely by actuation.

Numerous patents, patent applications and other literature have been cited throughout this disclosure. The contents of all citations are hereby expressly incorporated into this disclosure by reference.

Example 1

Actuable Scaffolds of Porous $\gamma$-$Fe_2O_3$/PLGA

Dispersions of $\gamma$-$Fe_2O_3$ particles in poly(D,L-lactide-co-glycolide) (PLGA) were prepared with concentrations ranging from 10 to 30 weight percent $\gamma$-$Fe_2O_3$ (based on PLGA) using chloroform as solvent. To form random open pore scaffolds, the $\gamma$-$Fe_2O_3$/PLGA/chloroform dispersion was mixed with sugar crystals to form a viscous paste. The paste was then packed in a Teflon mold of desired shape and size. The $\gamma$-$Fe_2O_3$/PLGA/sugar composite was then soaked in water for several hours to remove the porogen. The resulting porosity and interconnectivity were controlled by the amount of sugar added and the pore size was controlled by the sugar crystal size.

A typical pore morphology is illustrated in FIG. 5, which shows a line drawing of the surface of a random-pore $\gamma$-$Fe_2O_3$/PLGA scaffold material. Pores 500 are indicated as geometric shapes and the scaffold material 502 is indicated as the material between the pores 500. The random-pore $\gamma$-$Fe_2O_3$/PLGA scaffold material was fabricated into a cantilever beam. One end of the beam was fixed and upon application of a magnetic field using a small permanent magnet, the induced body forces caused the beam to deflect towards the magnet. The end deflection was greater than 5 mm for a beam of 10 mm in length and 1 mm in thickness. This result suggested strains of about 10% on the upper and lower surfaces of the beam in the length direction of the beam. The change in the appearance of the upper surface also suggested that individual pores changed shape and size during the macroscopic deflection Example 2

Simulation of Peristalsis in an Actuable Tube

Sheets of $\gamma$-$Fe_2O_3$/PLGA were formed with thicknesses ranging from 50 to 200 µm. The composite solution ($\gamma$-$Fe_2O_3$/PLGA/chloroform) was poured into a silicone mold and, after curing, pressed between heated Teflon coated metal plates in a Carver double-plate hydraulic press. A variety of three-dimensional structures may be fabricated from thin sheets by cutting, joining via melt-welding, and plastic shaping. Tubes were formed with variable diameter and length. With longer tubes, the deformation is localized to a short segment and will progress along the tube if the magnet is swept along the tube's axis. When a magnet was brought near such a tube, it deformed by being squashed down or drawn up out of its circular rest shape. Furthermore, when the tube was long relative to the diameter of the magnet and the magnet was passed along the length of the tube, an approximation of peristalsis was obtained because the deformation moved along the tube as a pulse. The moving pulse created a pumping action, sufficient to pump water (marked with a dye) at rates at least equal to those favored in cell growth.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall therebetween.

What is claimed is:

1. A selectively deformable structure comprising:
   a body portion having a longitudinal axis and being radially disposed at a pre-selected distance about said longitudinal axis, and extending substantially parallel to said longitudinal axis, the body portion having at least one chamber; and
   means for selectively deforming the body portion,
   wherein the structure is made from unmagnetized polymers and magnetic function is incorporated after the structure has been formed.

2. The structure of claim 1, wherein the body portion has at least two chambers.

3. A selectively deformable structure comprising:
   a body portion having a longitudinal axis and being radially disposed at a pre-selected distance about said longitudinal axis, and extending substantially parallel to said longitudinal axis, the body portion having at least two chambers; and
   means for selectively deforming the body portion, wherein said body portion comprises a magnetic material whose orientation of magnetization varies from one chamber to another.

4. The structure of claim 3, wherein the magnetic materials comprise iron oxide.

5. The structure of claim 2, wherein the chambers are arranged in a phased order such that they can be sequentially deformed.

6. The structure of claim 2, wherein the chambers are connected to form a closed loop.

7. The structure of claim 1, further comprising at least one aperture on said body portion.

8. The structure of claim 7, wherein the flow of materials through the aperture is regulated.

9. The structure of claim 1 wherein the magnetic function includes magnetic materials that include $Fe_2O_3$/PLGA.

10. The structure of claim 1, wherein the magnetic function is incorporated through ion exchange.

11. A selectively deformable structure comprising:
    a body portion having a longitudinal axis and a plurality of magnetically deformable plate-like sides joined together so as to be radially disposed about said longitudinal axis and extending substantially parallel to said longitudinal axis, the deformable plate-like sides forming at least two deformable chambers fluidly connected to one another, and the plate-like sides comprising a polymer having magnetic particles.

12. The selectively deformable structure of claim 11, wherein the polymer includes biocompatible polymer.

13. The selectively deformable structure of claim 11, wherein a first deformable plate-like side of the deformable plate-like sides has a first magnetic orientation and a second deformable plate-like side of the deformable plate-like sides has a second magnetic orientation different from the first magnetic orientation.

* * * * *